US011826563B2

(12) United States Patent
Grace

(10) Patent No.: US 11,826,563 B2
(45) Date of Patent: *Nov. 28, 2023

(54) EXPANDING TUBE COUPLING FOR REVERSIBLE LEAD LOCKING

(71) Applicant: SPECTRANETICS LLC, Colorado Springs (CO)

(72) Inventor: Kenneth P. Grace, Woodland Park, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/838,239

(22) Filed: Jun. 12, 2022

(65) Prior Publication Data

US 2022/0305257 A1   Sep. 29, 2022

Related U.S. Application Data

(63) Continuation of application No. 16/805,745, filed on Feb. 29, 2020, now Pat. No. 11,357,977, which is a continuation of application No. 15/856,355, filed on Dec. 28, 2017, now Pat. No. 10,576,274, which is a continuation-in-part of application No. 14/954,169, filed on Nov. 30, 2015, now Pat. No. 9,731,113.

(60) Provisional application No. 62/440,211, filed on Dec. 29, 2016, provisional application No. 62/098,214, filed on Dec. 30, 2014.

(51) Int. Cl.
*A61N 1/00* (2006.01)
*A61N 1/05* (2006.01)

(52) U.S. Cl.
CPC ............ *A61N 1/0587* (2013.01); *A61N 1/05* (2013.01); *A61N 1/059* (2013.01); *A61N 2001/0578* (2013.01)

(58) Field of Classification Search
CPC ........ A61N 1/0587; A61N 1/05; A61N 1/059; A61N 2001/0578
See application file for complete search history.

(56) References Cited

U.S. PATENT DOCUMENTS 1,891,497 A   12/1932   Birkenmaier
2,446,710 A   8/1948   Makaroff
(Continued)

FOREIGN PATENT DOCUMENTS

DE   19964093 B4   11/2001
EP   169784 A2   1/1986
(Continued)

OTHER PUBLICATIONS

Smith et al. Extraction of Transvenous Pacing and ICD Leads; Pace vol. 31 Jun. 2008 pp. 736-752.

*Primary Examiner* — Scott M. Getzow

(57) ABSTRACT

A device for extending a lead according to some embodiments includes a body, a tubular member coupled to the body, the tubular member comprising an outer surface, wherein the outer surface is sized to insert into an inner lumen of a lead, the tubular member is movable between a first configuration in which the tubular member slides into the lead, and a second configuration in which at least a portion of the tubular member expands to engage an inner surface of the lead; and, an actuation mechanism operatively coupled to the tubular member, the actuation mechanism configured to move the tubular member between the first configuration and second configuration.

15 Claims, 14 Drawing Sheets

(56) References Cited

U.S. PATENT DOCUMENTS

| | | |
|---|---|---|
| 2,615,402 A | 10/1952 | Chamberlain, Jr. |
| 2,627,137 A | 2/1953 | Koski |
| 2,856,933 A | 10/1958 | Allan et al. |
| 3,068,608 A | 12/1962 | Counts |
| 3,220,138 A | 11/1965 | Greenfield |
| 3,955,578 A | 5/1976 | Chamness et al. |
| 4,208,827 A | 6/1980 | Starkey |
| 4,250,653 A | 2/1981 | Davies |
| 4,471,777 A | 9/1984 | McCorkle, Jr. |
| 4,506,471 A | 3/1985 | Riead |
| 4,506,472 A | 3/1985 | Barman |
| 4,582,056 A | 4/1986 | McCorkle et al. |
| 4,636,346 A | 1/1987 | Gold et al. |
| 4,824,435 A | 4/1989 | Giesy et al. |
| 4,943,289 A | 7/1990 | Goode et al. |
| 4,988,347 A | 1/1991 | Goode et al. |
| 5,011,482 A | 4/1991 | Goode et al. |
| 5,013,310 A | 5/1991 | Goode et al. |
| 5,036,854 A | 8/1991 | Schollmeyer et al. |
| 5,098,440 A | 3/1992 | Hillstead |
| 5,163,938 A | 11/1992 | Kambara et al. |
| 5,171,233 A | 12/1992 | Amplatz et al. |
| 5,171,314 A | 12/1992 | Dulebohn |
| 5,192,286 A | 3/1993 | Phan |
| 5,207,683 A | 5/1993 | Goode et al. |
| 5,224,935 A | 7/1993 | Hollands |
| 5,247,942 A | 9/1993 | Prather et al. |
| 5,263,493 A | 11/1993 | Avitall |
| 5,282,478 A | 2/1994 | Fleischhaker et al. |
| 5,312,423 A | 5/1994 | Rosenbluth et al. |
| 5,342,371 A | 8/1994 | Welter et al. |
| 5,387,219 A | 2/1995 | Rappe |
| 5,417,684 A | 5/1995 | Jackson et al. |
| 5,443,472 A | 8/1995 | Li |
| 5,509,902 A | 4/1996 | Raulerson |
| 5,522,819 A | 6/1996 | Graves et al. |
| 5,555,883 A | 9/1996 | Avitall |
| 5,562,678 A | 10/1996 | Booker |
| 5,611,803 A | 3/1997 | Heaven et al. |
| 5,613,973 A | 3/1997 | Jackson et al. |
| 5,632,749 A | 5/1997 | Goode et al. |
| 5,637,098 A | 6/1997 | Bierman |
| 5,653,716 A | 8/1997 | Malo et al. |
| 5,681,347 A | 10/1997 | Cathcart et al. |
| 5,693,059 A | 12/1997 | Yoon |
| 5,697,936 A | 12/1997 | Shipko et al. |
| 5,769,858 A | 6/1998 | Pearson et al. |
| 5,782,839 A | 7/1998 | Hart et al. |
| 5,823,971 A | 10/1998 | Robinson et al. |
| 5,836,947 A | 11/1998 | Fleischman et al. |
| 5,868,754 A | 2/1999 | Levine et al. |
| 6,088,609 A | 7/2000 | Larison, II |
| 6,090,129 A | 7/2000 | Ouchi |
| 6,093,195 A | 7/2000 | Ouchi |
| 6,136,005 A | 10/2000 | Goode et al. |
| 6,167,315 A | 12/2000 | Coe et al. |
| 6,290,693 B1 | 9/2001 | Jung et al. |
| 6,375,639 B1 | 4/2002 | Duplessie et al. |
| 6,379,319 B1 | 4/2002 | Garibotto et al. |
| 6,432,115 B1 | 8/2002 | Mollenauer et al. |
| 6,478,777 B1 | 11/2002 | Honeck et al. |
| 6,500,182 B2 | 12/2002 | Foster |
| 6,511,492 B1 | 1/2003 | Rosenbluth et al. |
| 6,517,550 B1 | 2/2003 | Kónya et al. |
| 6,544,269 B2 | 4/2003 | Osborne et al. |
| 6,575,988 B2 | 6/2003 | Rousseau |
| 6,598,335 B2 | 7/2003 | Akhtar et al. |
| 6,687,548 B2 | 2/2004 | Goode |
| 6,695,813 B1 | 2/2004 | Boyle et al. |
| 6,712,826 B2 | 3/2004 | Lui |
| 6,743,228 B2 | 6/2004 | Lee et al. |
| 6,840,000 B2 | 1/2005 | Akhtar et al. |
| 6,893,450 B2 | 5/2005 | Foster |
| 7,041,108 B2 | 5/2006 | Lippitt et al. |
| 7,101,378 B2 | 9/2006 | Salameh et al. |
| 7,210,210 B2 | 5/2007 | Lippitt et |
| 7,359,756 B2 | 4/2008 | Goode |
| 7,470,256 B2 | 12/2008 | Lampropoulos et al. |
| 7,499,756 B2 | 3/2009 | Bowe et al. |
| 7,520,881 B2 | 4/2009 | Foushee et al. |
| 7,524,281 B2 | 4/2009 | Chu et al. |
| 7,641,646 B2 | 1/2010 | Kennedy, II |
| 7,651,503 B1 | 1/2010 | Coe et al. |
| 7,651,504 B2 | 1/2010 | Goode et al. |
| 7,713,275 B2 | 5/2010 | Greenberg et al. |
| 7,727,253 B2 | 6/2010 | Ackerman et al. |
| 7,731,693 B2 | 6/2010 | Melsheimer |
| 7,753,917 B2 | 7/2010 | Urbanski et al. |
| 7,753,918 B2 | 7/2010 | Hartley et al. |
| 7,758,592 B2 | 7/2010 | Ayala et al. |
| 7,776,052 B2 | 8/2010 | Greenberg et al. |
| 7,824,342 B2 | 11/2010 | Minosawa et al. |
| 7,871,414 B2 | 1/2011 | Hardin et al. |
| 7,993,359 B1 | 8/2011 | Atwell et al. |
| 8,070,693 B2 | 12/2011 | Ayala et al. |
| 8,109,986 B2 | 2/2012 | Styrc |
| 8,128,636 B2 | 3/2012 | Lui et al. |
| 8,137,291 B2 | 3/2012 | Melsheimer |
| 8,192,430 B2 | 6/2012 | Goode et al. |
| 8,252,019 B2 | 8/2012 | Fleming et al. |
| 8,323,179 B2 | 12/2012 | Chu et al. |
| 8,326,437 B2 | 12/2012 | Cully et al. |
| 8,469,970 B2 | 6/2013 | Diamant et al. |
| 8,551,139 B2 | 10/2013 | Surti et al. |
| 8,597,303 B2 | 12/2013 | Hammack et al. |
| 8,702,625 B2 | 4/2014 | Ayala et al. |
| 8,715,205 B2 | 5/2014 | Carter et al. |
| 8,740,969 B2 | 6/2014 | Jensen et al. |
| 8,747,295 B2 | 6/2014 | Chu et al. |
| 8,758,326 B2 | 6/2014 | Hennessy |
| 8,814,900 B2 | 8/2014 | Fleming et al. |
| 9,220,523 B2 | 12/2015 | Taylor et al. |
| 2002/0007204 A1 | 1/2002 | Goode |
| 2002/0010475 A1 | 1/2002 | Lui |
| 2002/0087100 A1 | 7/2002 | Onuki et al. |
| 2002/0107526 A1 | 8/2002 | Greenberg et al. |
| 2002/0123765 A1 | 9/2002 | Sepetka et al. |
| 2003/0036788 A1 | 2/2003 | Coe |
| 2003/0187457 A1 | 10/2003 | Weber |
| 2004/0116939 A1 | 6/2004 | Goode |
| 2004/0123765 A1 | 7/2004 | Furusawa et al. |
| 2004/0153096 A1 | 8/2004 | Goode et al. |
| 2004/0220604 A1 | 11/2004 | Fogarty |
| 2004/0243168 A1 | 12/2004 | Ferrera et al. |
| 2005/0043743 A1 | 2/2005 | Dennis |
| 2005/0096650 A1 | 5/2005 | Ouchi |
| 2005/0177022 A1 | 8/2005 | Chu et al. |
| 2005/0209609 A1 | 9/2005 | Wallace |
| 2006/0073904 A1 | 4/2006 | Novak |
| 2006/0100545 A1 | 5/2006 | Ayala et al. |
| 2006/0149295 A1 | 7/2006 | Fleming, III |
| 2007/0123804 A1 | 5/2007 | Ayala et al. |
| 2007/0191919 A1 | 8/2007 | Lui et al. |
| 2008/0147061 A1 | 6/2008 | Goode et al. |
| 2008/0147111 A1 | 6/2008 | Johnson et al. |
| 2008/0208075 A1 | 8/2008 | Goldenberg |
| 2008/0221587 A1 | 9/2008 | Schwartz |
| 2009/0112244 A1 | 4/2009 | Freudenthal |
| 2009/0234367 A1 | 9/2009 | Verma |
| 2010/0042107 A1 | 2/2010 | Merrifield |
| 2010/0252049 A1 | 10/2010 | Kost |
| 2011/0098720 A1 | 4/2011 | Taylor et al. |
| 2011/0106099 A1 | 5/2011 | Duffy et al. |
| 2011/0106107 A1 | 5/2011 | Binmoeller et al. |
| 2011/0112548 A1 | 5/2011 | Fifer et al. |
| 2011/0238078 A1 | 9/2011 | Goode et al. |
| 2012/0165827 A1 | 6/2012 | Khairkhahan et al. |
| 2012/0165850 A1 | 6/2012 | Deckard et al. |
| 2012/0310214 A1 | 12/2012 | Hennessy |
| 2013/0006261 A1 | 1/2013 | Lampropoulos et al. |
| 2013/0006262 A1 | 1/2013 | Lampropoulos et al. |
| 2013/0131688 A1 | 5/2013 | Schwartz |
| 2013/0172714 A1 | 7/2013 | Li et al. |
| 2013/0184738 A1 | 7/2013 | Laroya et al. |

(56) References Cited

U.S. PATENT DOCUMENTS

| | | |
|---|---|---|
| 2013/0184741 A1 | 7/2013 | Laroya et al. |
| 2013/0197476 A1 | 8/2013 | Karpiel |
| 2013/0238024 A1 | 9/2013 | Taylor et al. |
| 2013/0261638 A1 | 10/2013 | Diamant et al. |
| 2014/0155930 A1 | 6/2014 | Bennett et al. |
| 2014/0171960 A1 | 6/2014 | Goode |
| 2014/0188124 A1 | 7/2014 | Lampropoulos et al. |
| 2014/0296905 A1 | 10/2014 | Dela |
| 2014/0350566 A1 | 11/2014 | Emmanouilidis |
| 2014/0350593 A1 | 11/2014 | Laroya et al. |
| 2016/0183954 A1 | 6/2016 | Taylor et al. |
| 2016/0184579 A1 | 6/2016 | Triffo |
| 2016/0184580 A1 | 6/2016 | Grace |

FOREIGN PATENT DOCUMENTS

| | | |
|---|---|---|
| EP | 0174930 A1 | 3/1986 |
| EP | 0368568 B1 | 5/1990 |
| EP | 0661949 A1 | 7/1995 |
| EP | 0688184 A1 | 12/1995 |
| EP | 0708621 B1 | 5/1996 |
| EP | 0733382 A2 | 9/1996 |
| EP | 0733383 A2 | 9/1996 |
| EP | 1043042 B1 | 10/2000 |
| EP | 1063926 B1 | 1/2001 |
| EP | 1251787 B1 | 10/2002 |
| EP | 1284782 B1 | 2/2003 |
| EP | 1317214 B1 | 6/2003 |
| EP | 1330194 B1 | 7/2003 |
| EP | 1572282 B1 | 9/2005 |
| EP | 1587573 B1 | 10/2005 |
| EP | 1722696 A1 | 11/2006 |
| EP | 1757234 B1 | 2/2007 |
| EP | 1793886 B1 | 6/2007 |
| EP | 1815811 B1 | 8/2007 |
| EP | 1848497 B1 | 10/2007 |
| EP | 1951350 B1 | 8/2008 |
| EP | 1984056 A1 | 10/2008 |
| EP | 1984072 A2 | 10/2008 |
| EP | 1996089 B1 | 12/2008 |
| EP | 2054116 B1 | 5/2009 |
| EP | 2094178 B1 | 9/2009 |
| EP | 2124766 B1 | 12/2009 |
| EP | 2240126 B1 | 10/2010 |
| EP | 2349026 B1 | 8/2011 |
| EP | 2375997 B1 | 10/2011 |
| EP | 2489313 A1 | 8/2012 |
| EP | 2493392 B1 | 9/2012 |
| EP | 2496151 A2 | 9/2012 |
| EP | 2552327 A1 | 2/2013 |
| EP | 2659841 A2 | 11/2013 |
| EP | 2661233 A1 | 11/2013 |
| EP | 2661288 A1 | 11/2013 |
| EP | 2731513 A1 | 5/2014 |
| EP | 2740437 A1 | 6/2014 |
| EP | 2742871 B1 | 6/2014 |
| EP | 2783658 A2 | 10/2014 |
| EP | 2802276 A1 | 11/2014 |
| WO | 1996028101 A1 | 9/1996 |
| WO | 2001056484 A1 | 8/2001 |
| WO | 2001087412 A2 | 11/2001 |
| WO | 2002022028 A2 | 3/2002 |
| WO | 2005084563 A1 | 9/2005 |
| WO | 2007095252 A1 | 8/2007 |
| WO | 2007100474 A2 | 9/2007 |
| WO | 2008045143 A2 | 4/2008 |
| WO | 2008112608 A2 | 9/2008 |
| WO | 2010002549 A2 | 1/2010 |
| WO | 2011032157 A1 | 3/2011 |
| WO | 2011053645 A1 | 5/2011 |
| WO | 2011123342 A1 | 10/2011 |
| WO | 2012006247 A1 | 1/2012 |
| WO | 2013106713 A1 | 7/2013 |
| WO | 2014080338 A1 | 5/2014 |
| WO | 2014145598 A1 | 9/2014 |

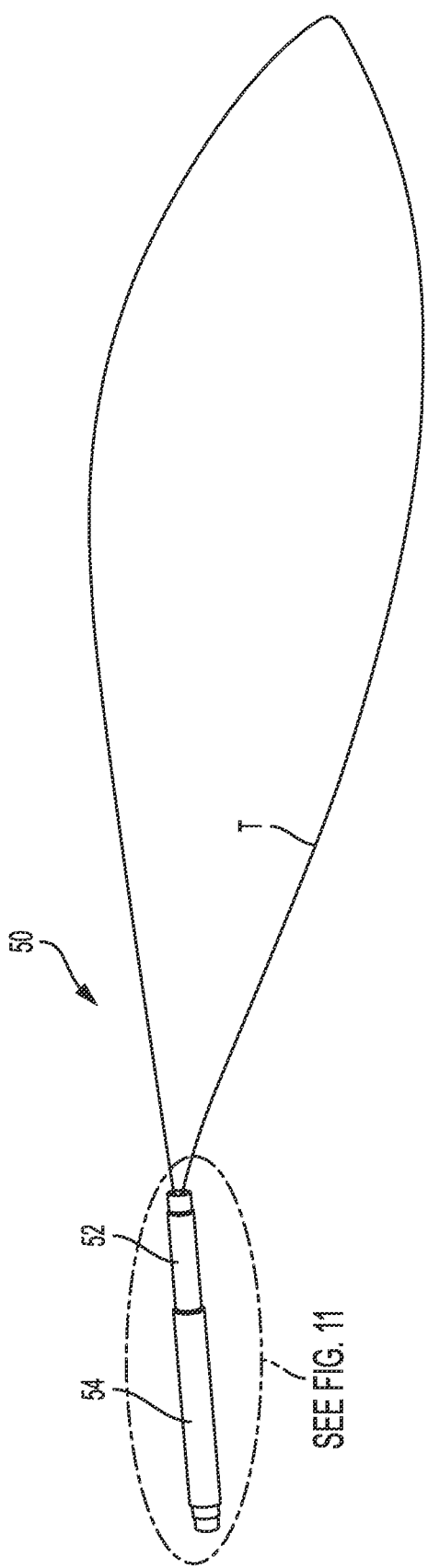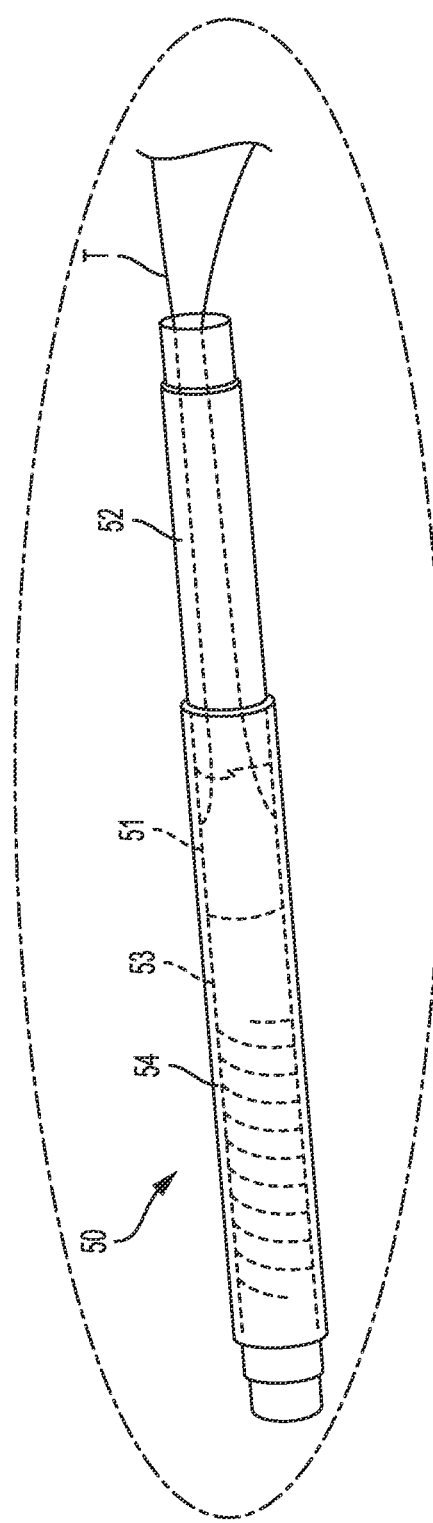

EXPANDING TUBE COUPLING FOR REVERSIBLE LEAD LOCKING

CROSS-REFERENCE TO RELATED APPLICATION

The present application is a continuation of U.S. application Ser. No. 16/805,745, filed Feb. 29, 2020, entitled EXPANDING COIL COUPLING FOR LEAD EXTENSION AND EXTRACTION, now U.S. Pat. No. 11,357,977, which is a continuation of U.S. application Ser. No. 15/856,355, filed Dec. 28, 2017, entitled EXPANDING COIL COUPLING FOR LEAD EXTENSION AND EXTRACTION, now U.S. Pat. No. 10,576,274, which claims the benefit of and priority to, under 35 U.S.C. § 119(e), U.S. Provisional Application Ser. No. 62/440,211, filed Dec. 29, 2016, entitled EXPANDING TUBE COUPLING FOR REVERSIBLE LEAD LOCKING, which are all hereby incorporated by reference in their entirety for all purposes. U.S. application Ser. No. 15/856,355 is also a continuation-in-part of U.S. application Ser. No. 14/954,169, filed Nov. 30, 2015, entitled COLLAPSING COIL COUPLING FOR LEAD EXTENSION AND EXTRACTION, now U.S. Pat. No. 9,731,113, which claims the benefit of and priority to, under 35 U.S.C. § 119(e), U.S. Provisional Application Ser. No. 62/098,214, filed Dec. 30, 2014, entitled COLLAPSING COIL COUPLING FOR LEAD EXTENSION AND EXTRACTION, which are all hereby incorporated by reference in their entirety for all purposes.

FIELD OF THE DISCLOSURE

The present disclosure relates generally to lead extension and lead locking, and more specifically to methods and devices for extending within a lead and/or locking within a lead to provide structure over which a lead extraction device may be passed.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat according to a healthy rhythm. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. The body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature. Typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin and the surrounding tissue is notably fibrous.

A variety of tools have been developed to make lead extraction safer and more successful. Current lead extraction techniques include mechanical traction, mechanical devices, and laser devices. Extracting a lead may often involve applying tension to the lead while it is still implanted, whether in order to pull it free using the tension force, to loosen it, and/or to apply an extraction device over the lead. Applying an extraction device over a lead which is not adequately tensioned may result in kinking or damage to the lead, for example at locations which are not as easy to access as the proximal portion of the lead that was near to or coupled with the pacemaker or defibrillator. In extracting a lead, the lead (including any conductive portions, insulating sheath, and/or casing layers) is often cut between the distal end of the lead and the proximal end of the lead (which is often coupled to the pacemaker). In other situations, the lead exhibits structural failure, either before, or during, the lead extraction surgical intervention. These situations may result in a lead that is not as long as the clinician would like it to be in order to both apply tension to the lead and/or deploy an extraction device over the lead. Existing lead extension technologies may be limited in the maximum level of tension which they can support in coupling with the lead, with the reversibility of such coupling, and/or with the reliability of such coupling.

SUMMARY

A device for extending a lead according to embodiments of the present disclosure includes a body; a coil element coupled to the body, the body configured to cover at least a portion of the coil element during use, the coil element including a plurality of coils forming an inner lumen, wherein the inner lumen is sized to receive an outer surface of a lead, the coil element is movable between a first configuration in which the coil element slides over the lead, and a second configuration in which at least some coils of the plurality of coils grip the outer surface of the lead; an actuation mechanism operatively coupled to the coil element, the actuation mechanism configured to move the coil element between the first and second configurations; and a tether coupled to the lead via one or more of the body, the coil element, and the actuation mechanism, the tether configured to extend further proximally than a proximal-most end of the lead, the tether further configured to transfer at least a portion of a tension force applied to the tether to the lead via the one or more of the body, the coil element, and the actuation mechanism.

In some cases, the actuation mechanism includes a first ratchet grip and a second ratchet grip, wherein the first ratchet grip is coupled to a first end of the coil element, wherein the second ratchet grip is coupled to a second end of the coil element, and wherein the actuation mechanism is configured to move the coil element between the first and second configurations via one or both of rotation of the first ratchet grip along a first rotational direction relative to the second ratchet grip, and rotation of the second ratchet grip along a second rotational direction relative to the first ratchet grip, wherein the first and second rotational directions are opposing rotational directions.

In some cases, the first ratchet grip engages the second ratchet grip at a unidirectional rotational coupling that permits rotation of the first ratchet grip along the first rotational direction relative to the second ratchet grip and rotation of the second ratchet grip along the second rotational direction relative to the first ratchet grip while inhibiting rotation of the first ratchet grip along the second rotational direction relative to the second ratchet grip and of the second ratchet grip along the first rotational direction relative to the first ratchet grip while the first ratchet grip is in the unidirectional rotational coupling with the second ratchet grip. The unidirectional rotational coupling may include one or more undercut or back-cut teeth formed on one or both of the first and second ratchet grips. A safety cap may be used and configured to cover the unidirectional rotational coupling.

In some cases, the first and second ratchet grips are axially separable from one another to release the unidirectional rotational coupling, thereby permitting the coil element to move from the second configuration to the first configuration.

Embodiments of such devices may further include an outer sleeve, a keyway formed in one of the outer sleeve and the first ratchet grip, and a tab formed in the other of the outer sleeve and the first ratchet grip, wherein torque is transmitted from the outer sleeve to the first ratchet grip via an interface between the keyway and the tab, the tab configured to break away from the outer sleeve at a level of applied torque.

In some cases, the actuation mechanism is itself the body or forms all or part of the body. In some embodiments, the body includes a first sleeve and a second sleeve, wherein the first sleeve is coupled to a first end of the coil element, wherein the second sleeve is coupled to a second end of the coil element, and wherein the actuation mechanism is configured to move the coil element between the first and second configurations via axial translation of the first sleeve along a direction relative to the second sleeve. The actuation mechanism may further include a pin coupled to one of the first and second sleeves and a slot formed in another of the first and second sleeves, wherein the slot guides a path of translation of the first sleeve with respect to the second sleeve.

In some cases, the slot includes a portion that imparts a tightening twist to the coil element in moving the coil element to the second configuration. The slot may further include a portion that causes translation of the first sleeve along a second direction relative to the second sleeve in moving the coil element to the second configuration, wherein the second direction is different from and/or opposite to the first direction.

According to some embodiments of the present disclosure, the plurality of coils include coils of different pitch, such that some of the plurality of coils are configured to collapse to grip the lead at a lower applied torque than others of the plurality of coils.

A method for extending a lead according to some embodiments of the present disclosure includes sliding a coil element over a lead when the coil element is in a first configuration, the coil element comprising a plurality of coils forming an inner lumen sized to receive an outer surface of the lead; moving the coil element from the first configuration into a second configuration in which at least some coils of the coil element grip the outer surface of the lead; and applying tension to the lead by applying tension to a tether that is coupled to the lead via the coil element when the coil element is in the second configuration.

An additional device for extending a lead or a lead locking device according to embodiments of the present disclosure includes a body, a tubular member coupled to the body, the tubular member comprising an outer surface, wherein the outer surface is sized to insert into an inner lumen of a lead, the tubular member is movable between a first configuration in which the tubular member slides into the lead, and a second configuration in which at least a portion of the tubular member expands to engage an inner surface of the lead, and an actuation mechanism operatively coupled to the tubular member, the actuation mechanism configured to move the tubular member between the first configuration and second configuration.

A device wherein the tubular member comprises a plurality of segments.

A device wherein at least some segments of the plurality of segments springably release to sequentially engage the inner surface of the lead from a distal-most end of the lead to a proximal-most end of the lead.

A device wherein at least some segments of the plurality of segments springably release to sequentially engage the inner surface of the lead from a proximal-most end of the lead to a distal-most end of the lead.

A device further comprising a tether coupled to the lead via one or more of the body, the tubular member, and the actuation mechanism, the tether configured to extend further proximally than a proximal-most end of the lead, the tether further configured to transfer at least a portion of a tension force applied to the tether to the lead via the one or more of the body, the tubular member, and the actuation mechanism.

A device wherein the actuation mechanism comprises a first ratchet grip and a second ratchet grip, wherein the first ratchet grip is coupled to a first end of the tubular member, wherein the second ratchet grip is coupled to a second end of the tubular member, and wherein the actuation mechanism is configured to move the tubular member between the first and second configurations via one or both of: rotation of the first ratchet grip along a first rotational direction relative to the second ratchet grip, and rotation of the second ratchet grip along a second rotational direction relative to the first ratchet grip, wherein the first and second rotational directions are opposing rotational directions.

A device wherein the first ratchet grip engages the second ratchet grip at a unidirectional rotational coupling that permits rotation of the first ratchet grip along the first rotational direction relative to the second ratchet grip and rotation of the second ratchet grip along the second rotational direction relative to the first ratchet grip while inhibiting rotation of the first ratchet grip along the second rotational direction relative to the second ratchet grip and of the second ratchet grip along the first rotational direction relative to the first ratchet grip while the first ratchet grip is in the unidirectional rotational coupling with the second ratchet grip.

A device wherein the unidirectional rotational coupling includes one or more undercut or back-cut teeth formed on one or both of the first and second ratchet grips.

A device wherein the first and second ratchet grips are axially separable from one another to release the unidirectional rotational coupling, thereby permitting the tubular member to move from the second configuration to the first configuration.

A device further comprising an inner sleeve, a keyway formed in one of the inner sleeve and the first ratchet grip, and a tab formed in the other of the inner sleeve and the first ratchet grip, wherein torque is transmitted from the inner sleeve to the first ratchet grip via an interface between the keyway and the tab, the tab configured to break away from the inner sleeve at a level of applied torque.

A device wherein the actuation mechanism is the body.

A device wherein the body comprises a first sleeve and a second sleeve, wherein the first sleeve is coupled to a first end of the tubular member, wherein the second sleeve is coupled to a second end of the tubular member, and wherein the actuation mechanism is configured to move the tubular member between the first and second configurations via axial translation of the first sleeve along a direction relative to the second sleeve.

A device wherein the actuation mechanism further comprises a pin coupled to one of the first and second sleeves and a slot formed in another of the first and second sleeves, wherein the slot guides a path of translation of the first sleeve with respect to the second sleeve.

A device wherein the slot includes a portion that imparts a tightening twist to the tubular member in moving the tubular member to the second configuration.

A device wherein the direction is a first direction, and wherein the slot includes a portion that causes translation of the first sleeve along a second direction relative to the second sleeve in moving the tubular member to the second configuration, wherein the second direction is different from the first direction.

A device wherein the second direction is opposite to the first direction.

A device wherein the plurality of segments include segments of different pitch, such that some of the plurality of segments are configured to expand to springably engage the lead at a lower applied torque than others of the plurality of segments.

An additional method for extending a lead or locking onto an interior of a lead includes sliding a tubular member into a lead when the tubular member is in a first configuration, the tubular member comprising an outer surface sized to insert into an inner lumen of the lead, moving the tubular member from the first configuration into a second configuration in which at least a portion of the tubular member expands to engage the inner lumen of the lead by actuating an actuation mechanism operatively coupled to the tubular member, the actuation mechanism configured to move the tubular member between the first configuration and the second configuration.

The method wherein the tubular member comprises a plurality of segments.

The method wherein at least some segments of the plurality of segments springably release to sequentially engage the inner surface of the lead from a distal-most end of the lead to a proximal-most end of the lead or from a proximal-most end of the lead to a distal-most end of the lead.

The method wherein the actuation mechanism comprises a first ratchet grip and a second ratchet grip, wherein the first ratchet grip is coupled to a first end of the tubular member, wherein the second ratchet grip is coupled to a second end of the tubular member, and wherein manipulating the actuation mechanism to move the tubular member from the first configuration into the second configuration includes one or both of: rotating the first ratchet grip along a first rotational direction relative to the second ratchet grip, and rotating the second ratchet grip along a second rotational direction relative to the first ratchet grip, wherein the first and second rotational directions are opposing rotational directions.

The method wherein the tubular member includes a first end coupled to a first sleeve and a second end coupled to a second sleeve, and wherein manipulating the actuation mechanism to move the tubular member from the first configuration into the second configuration includes translating the first sleeve along a direction relative to the second sleeve.

The method wherein the actuation mechanism further comprises a pin coupled to one of the first and second sleeves and a slot formed in another of the first and second sleeves, the slot guiding a path of translation of the first sleeve with respect to the second sleeve, and wherein manipulating the actuation mechanism to move the tubular member from the first configuration into the second configuration causes the slot to impart a releasing twist to the tubular member.

The method wherein the plurality of segments include segments of a first pitch and segments of a second pitch, and moving the tubular member from the first configuration into the second configuration includes releasing the segments of the first pitch to springably engage the inner lumen of the lead at a first applied torque and releasing the segments of the second pitch to springably engage the inner lumen of the lead at a second applied torque, the second applied torque being less than the first applied torque.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "lead" is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate possible and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 10 illustrates a front elevation view of a ratchet body actuation mechanism for a coil element, according to an embodiment of the present disclosure.

FIG. 11 illustrates a front detail view of the ratchet body actuation mechanism within line 11-11 of FIG. 10 and with internal components illustrated in dashed lines, according to an embodiment of the present disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
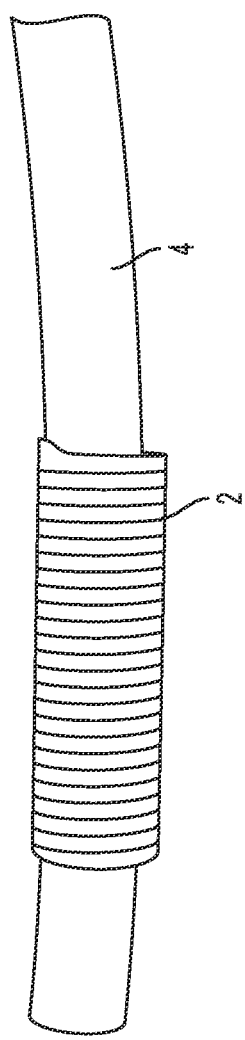
FIG. 1 illustrates a top plan view of a coil element in a configuration for sliding over a lead, according to an embodiment of the present disclosure.

FIG. 1 illustrates a top plan view of a coil element 2 (which may also be referred to as a hypotube) in a configuration for sliding over a lead 4, according to an embodiment of the present disclosure. In the configuration of FIG. 1, the coil element 2 includes a plurality of coils, and an inner lumen with an inner dimension or diameter that is large enough to accept the lead 4 therethrough, such that the coil element 2 may be placed over the lead 2 and/or slide freely over the lead. The segment of coil element 2 depicted may be a segment of a laser cut hypotube with an interrupted spiral cut ("ISC") pattern. The plurality of coils may be formed by, for example, ISC, coil cut pattern, and/or the like. The coil element 2 may be deformed from the configuration shown in FIG. 1 to the configuration shown in FIG. 2 in which some or all of the plurality of coils of the coil element 2 are compressed or deformed such that they engage and grip with the outer surface of the lead 4. In some embodiments, the deformation of the coil element 2 results in compressive force being applied to the lead 4.

The coil element 2 may be moved between a first configuration in which the coil element 2 slides over the lead 4 to a second configuration in which some or all of the coils of the coil element 2 grippingly engage the outer surface of the lead in various ways. As one example, the coil element 2 may be longitudinally pulled or stretched, thereby causing the inner diameter of the coils to shrink to the point at which the coil engages the lead 4. As another example, one end of the coil element 2 may be rotated, twisted, or turned with respect to the other end of the coil element 2 in order to cause a tightening of the windings of the coils of the coil element 2, thereby shrinking their inner diameters to the point at which the coil engages the lead 4.

Figure 2:
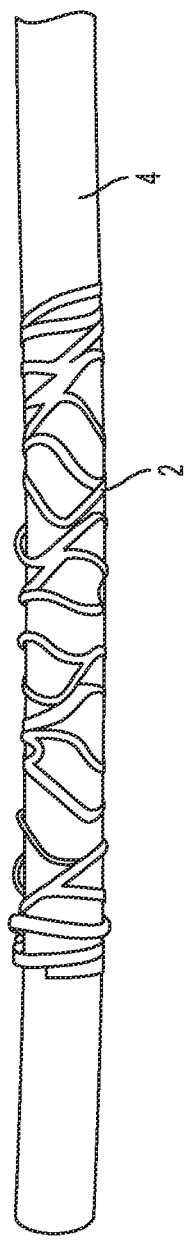
FIG. 2 illustrates a top plan view of the coil element of FIG. 1 in a different configuration in which the coils of the coil element engage the outer surface of the lead, according to an embodiment of the present disclosure.

FIG. 2 illustrates the coil element 2 in a deformed configuration, in which the deformed laser cut segment with ISC cut pattern has been deformed over the lead 4. The coil element 2 has been deformed in order to transform it into a traction tool. A trailing wire or tether (not shown), including for example high strength braided fibers, metal wires, and the like, may be attached to the coil element 2 to allow tension to be applied to the coil element 2 from a control point away from the coil element 2 and lead 4 itself.

Figure 3:
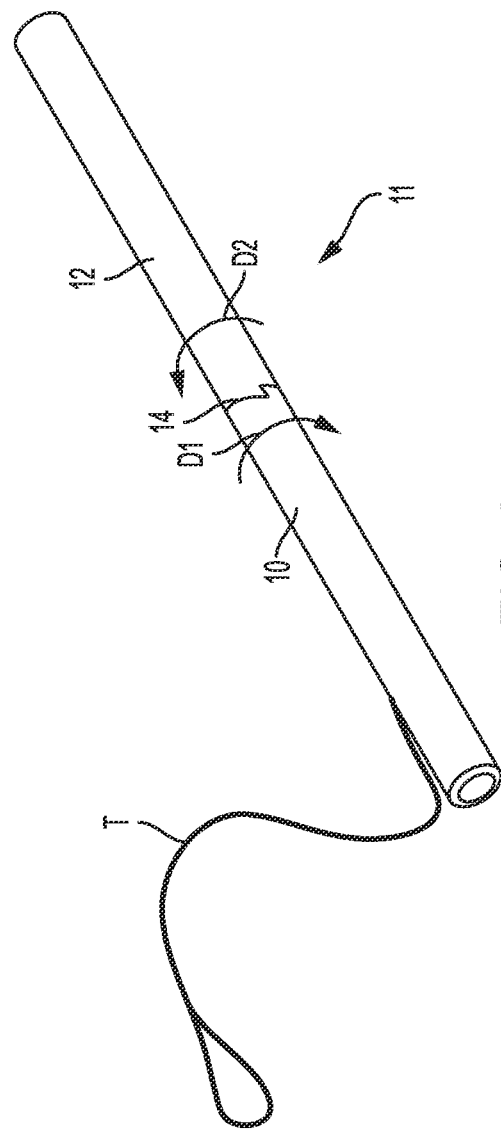
FIG. 3 illustrates a perspective view of a ratchet body actuation mechanism for a coil element, according to an embodiment of the present disclosure.
Figure 4:
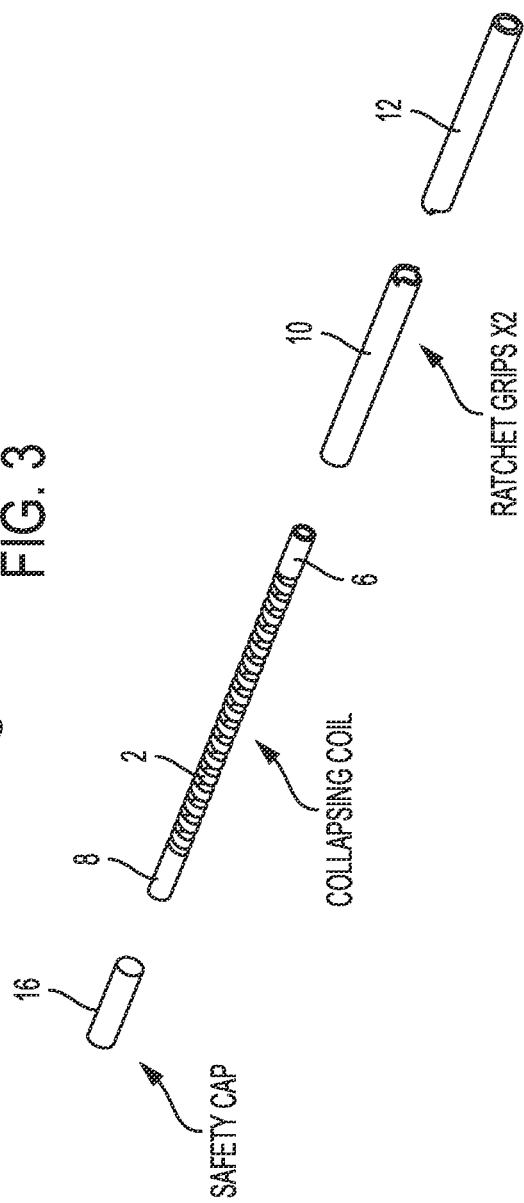
FIG. 4 illustrates an exploded view of the ratchet body actuation mechanism of FIG. 3, according to an embodiment of the present disclosure.

FIGS. 3 and 4 illustrate one embodiment of a ratchet deployment device 11, with an internal coil cut coil element 2 and ratchet grips 10, 12. In the embodiment shown in FIGS. 3 and 4, ratchet grip 10 is coupled to end 8 of coil element 2 (e.g. by welding), and ratchet grip 12 is coupled to end 6 of coil element 2 (e.g. by welding). Ratchet grips 10 and 12 interface with each other at unidirectional rotational coupling 14, which may be formed by teeth or other interengaging projections and indentations which permit ratchet grip 10 to rotate in direction D1 with respect to ratchet grip 12, and which permit ratchet grip 12 to rotate in direction D2 with respect to ratchet grip 10, but which inhibit rotation of such ratchet grips in respective directions opposite to those of D1 and D2 when the ratchet grips 10 and 12 are engaged with one another. In some embodiments, the first and second ratchet grips 10, 12 are biased toward one another, for example by the coil element 2 acting as a spring. In other embodiments, the first and second ratchet grips 10, 12 are not biased together, but remain in place against one another based on the ability of the coil element 2 to reduce its inner diameter as it is twisted without elongating. The unidirectional rotational coupling mechanism may be referred to, in some cases, as a ratchet mechanism. The ratchet mechanism may be formed by teeth that are formed or cut into the ends of the ratchet grips 10, 12; such teeth may be undercut and/or back-cut, for example.

According to some embodiments of the present disclosure, the unidirectional rotational coupling is reversible and/or releasable. For example, for a coil element 2 that has undergone elastic deformation in moving to the gripping configuration, pulling apart the first and second ratchet grips 10, 12 and then releasing one or both ratchet grips 10, 12 permits the coil element 2 to unwind and release its grip from the lead 4. A safety cap 16 may be included on the device 11, for example slid or otherwise positioned over the location of the unidirectional rotational coupling 14. The safety cap 16 prevents the mechanisms (e.g. teeth) of the unidirectional rotational coupling 14 from snagging or damaging surrounding tissue, whether during primary rotation/tightening or during release of the unidirectional rotational coupling 14.

When the coil element 2 is moved to the configuration in which it engages the lead 4, the coil element 2 creates a relatively large force on the lead 4 over a large area. As the two ratchet grips 10, 12 are pulled apart, the coil element 2 may release the lead 4 and the device 11 can be repositioned and re-tightened on the lead 4 body. Additionally, this embodiment may include a safety cap 16 that protects the physician's hands from the ratchet mechanism 14. This cap 16 may be attached to one of the ratchets 10, 12 at one end via weld joints, and may float over the ratchet mechanism 14.

A tether T may be coupled to the body, for example to one of the first and second ratchet grips. As shown in FIG. 3, a tether T is coupled to the ratchet grip 10 (length of tether T is not necessarily to scale). Tether T extends further proximally than the lead when the device 11 is coupled with the lead. Tension applied to tether T is transmitted to the device 11 and thus to the lead when the device 11 is coupled to the lead. Tether T also permits an extraction device to be placed over it and advanced over the tether T to the device 11 and eventually to the lead to which device 11 is attached.

Figure 5:
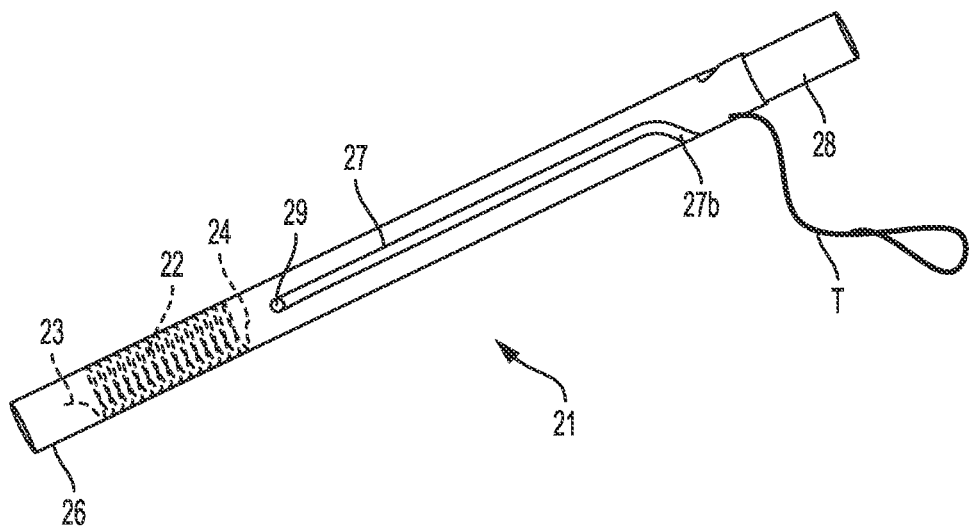
FIG. 5 illustrates a front perspective view of a cam actuation mechanism for a coil element, according to an embodiment of the present disclosure.
Figure 6:
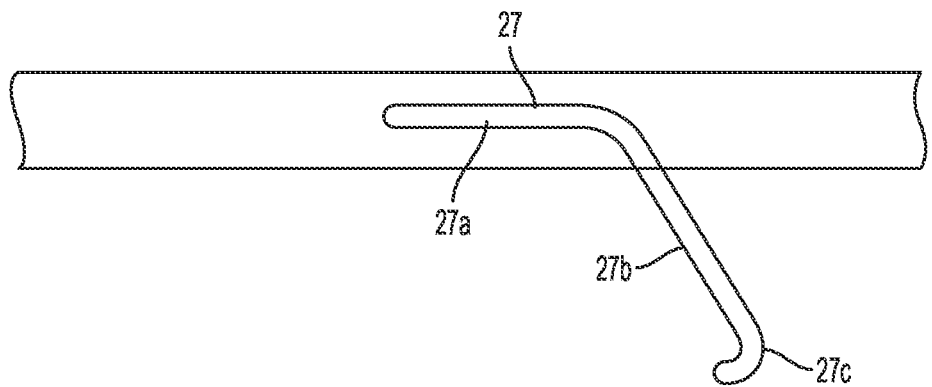
FIG. 6 illustrates a partial front elevation view of the cam actuation mechanism of FIG. 5 showing an unwound and flattened depiction of the cam pathway, according to an embodiment of the present disclosure.

FIG. 5 illustrates a front perspective view of a cam actuation mechanism device 21 for a coil element 22, according to an embodiment of the present disclosure. FIG. 6 illustrates a partial front elevation view of the cam actuation mechanism device 21 of FIG. 5 showing an unwound and flattened depiction of the cam pathway 27, according to an embodiment of the present disclosure. The device 21 includes a coil element 22, which may in some embodiments include features and characteristics that are the same as or similar to coil element 2. Device 21 includes a body formed by an outer sleeve 26 and an inner sleeve 28; coil element 22 is coupled to outer sleeve 26 at end 23 (e.g. by welding), and coil element 22 is coupled to inner sleeve 28 at end 24 (e.g. by welding).

During operation, the coil element 22 is placed over a lead, for example by placing the distal end 23 of coil element 22 over the lead. In this first configuration, the coil element 22 has coils that have an inner diameter that is larger than the outer diameter of the outer surface of the lead over which it is placed. Next, the coil element 22 may be moved to a second configuration in which some or all of the coils of the coil element 22 are engaged in a gripping manner with the outer surface of the lead. This may be accomplished by stretching the coil element 22 longitudinally, for example along a longitudinal axis of the coil element 22, which may be aligned with the longitudinal axis of the device 21 and the lead onto which the device 21 is attached. In the embodiment shown in FIG. 5, the longitudinal stretching of the coil element 22 is achieved by translating the outer sleeve 28 away from the inner sleeve 26. The movement of the inner sleeve 26 with respect to the outer sleeve 28 may be governed by a cam actuation mechanism. The cam actuation mechanism of FIGS. 5 and 6 takes the form of a cam pathway 27 formed into the outer sleeve 26, within which is guided a pin 29 coupled to the inner sleeve 28. The cam pathway 27 may be formed of a slot extending through the outer sleeve 26 and/or of a groove formed within an inner surface of the outer sleeve 26, according to an embodiment of the present disclosure.

The cam pathway 27 may include various sections to achieve lengthening, compression, and/or twisting of the coil element 22, according to embodiments of the present disclosure. While one example of a cam pathway 27 is provided, one of ordinary skill in the art, who is familiar with the present disclosure, will appreciate the numerous possible cam pathways in order to move a coil element 22 to a gripping engagement with a lead. Cam pathway 27 includes a first section 27*a* that extends along a substantially straight line that is substantially parallel to a longitudinal axis of the coil element 22 and outer and inner sleeves 26, 28. A second section 27*b* generally continues to extend in a direction away from the coil element 22, while also wrapping around the outer sleeve 26 in order to cause the inner sleeve 28 to twist or turn relative to the outer sleeve 26. A third section 27*c* causes the pin 29 to move back toward the coil element 22 while continuing to cause twisting of the inner sleeve 28 relative to the outer sleeve 26. According to some embodiments, the inner sleeve 26 is biased toward the outer sleeve 28 such that this biasing force is overcome when it is desired to pull them apart (thereby moving the coil element 22 to the second/lead engaging position). Section 27*c* of the cam pathway 27 provides an endpoint in the second configuration in which the pin 29 can rest and in which the pin 29 is deterred from sliding back down the pathway sections 27*b* and 27*a* due to the biasing, according to an embodiment of the present disclosure. In this manner, Section 27*c* forms a locking mechanism which locks the pin 29 in the ending position and thereby locks the coil element 22 in a configuration in which it is engaged in a gripping configuration with the lead.

Also, while end 23 of coil element 22 is described above as a distal end, the entire device 21 may alternatively be placed over and engaged with the lead in the opposite direction, for example by placing the lead through the sleeve 28, then sleeve 26 and then end 24 of coil element 22, according to an embodiment of the present disclosure. Furthermore, while the pin 29 is described above as being coupled with inner sleeve 28 and the cam pathway 27 is described as being formed in outer sleeve 26, the pin 29 may alternatively be coupled to the outer sleeve 26 and the cam pathway 27 may alternatively be formed in the inner sleeve 28, according to an embodiment of the present disclosure.

A tether T may be coupled to the body, for example to the outer sleeve 26, according to an embodiment of the present disclosure. As shown in FIG. 5, a tether T is coupled to the outer sleeve 26 (length of tether T is not necessarily to scale). Tether T extends further proximally than the lead when the device 21 is coupled with the lead. Tension applied to tether T is transmitted to the device 21 and thus to the lead when the device 21 is coupled to the lead. Tether T also permits an extraction device to be placed over it and advanced over the tether T to the device 21 and eventually to the lead to which device 21 is attached.

Figure 7:
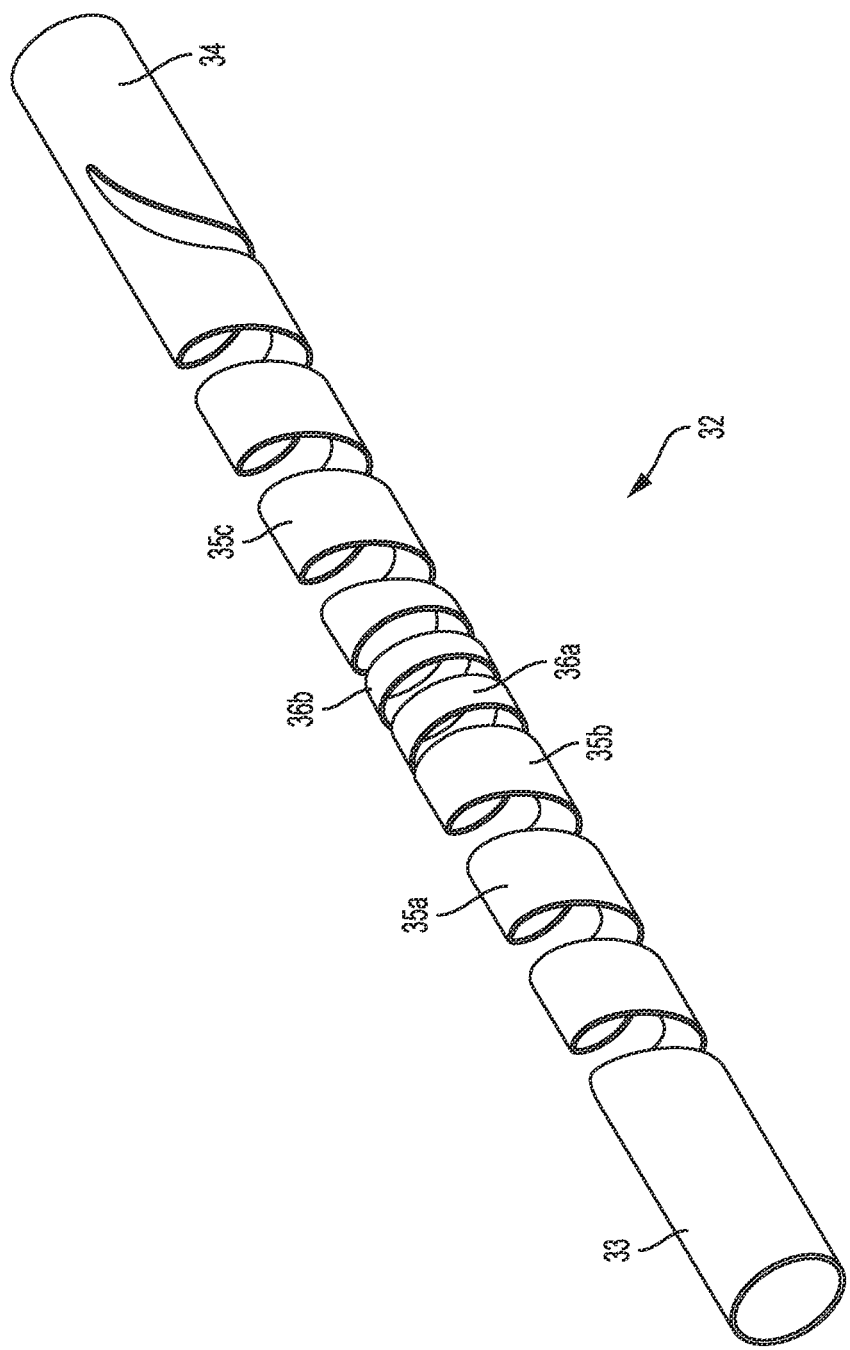
FIG. 7 illustrates an alternative coil element, according to an embodiment of the present disclosure.

FIG. 7 illustrates a coil element 32 with a particular geometry for achieving selective tightening about a lead, according to an embodiment of the present disclosure. Coil element 32 includes a variable pitch coil; the coil element 32 includes a tight pitch segment with tight pitch coils 36*a*, 36*b* and loose pitch segments 35*a*, 35*b*, and 35*c*. When a torque is applied to twist or rotate the first end 33 and second end 34 with respect to each other, the tight pitch coils 36 will deform or tighten onto the lead first, followed by the loose pitch segments 35 at higher torque. The variable pitch coil element 32 may be positioned over leads having multiple different types of components, for example insulation and high voltage cables, by positioning the appropriate pitch segment 35, 36 over the desired area or type of component on the lead.

Figure 8:
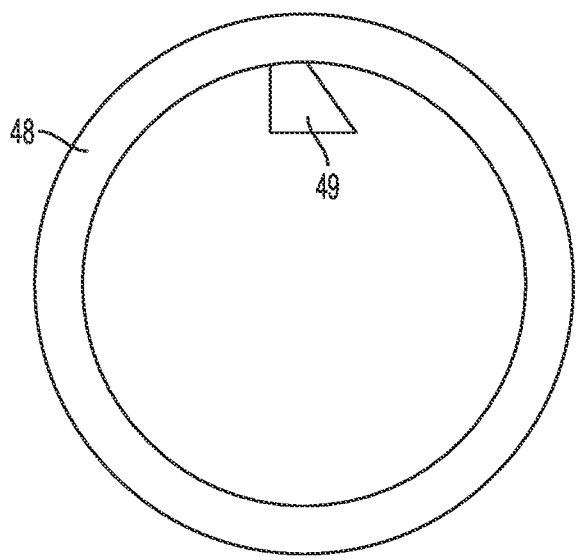
FIG. 8 illustrates a side elevation view of an outer sleeve with a breakaway torque tab, according to an embodiment of the present disclosure.
Figure 9:
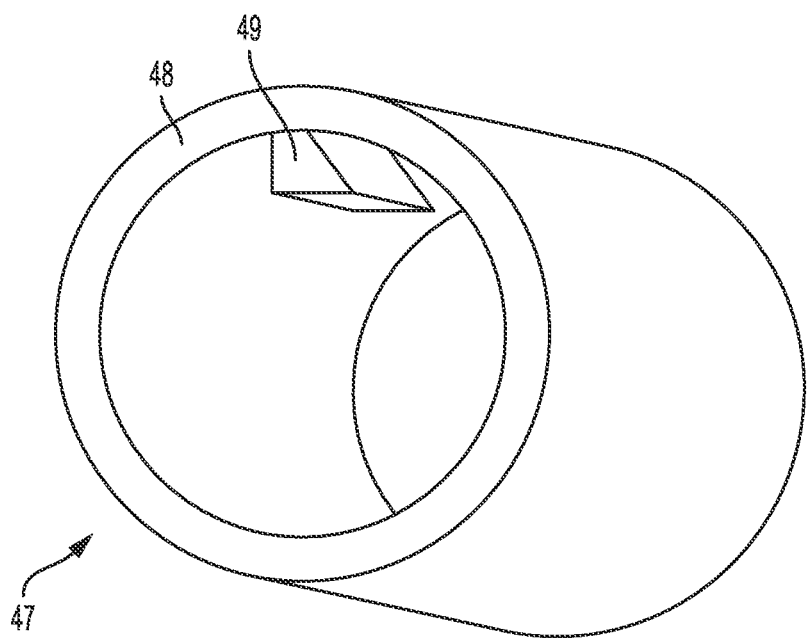
FIG. 9 illustrates a side and front perspective view of the outer sleeve of FIG. 8, according to an embodiment of the present disclosure.

FIGS. 8 and 9 illustrate an outer sleeve 48 with a breakaway torque tab 49, according to an embodiment of the present disclosure. The outer sleeve 48 may be used with a rotational-based embodiment of a device with a coil element, for example with the device 11 described above. Outer sleeve 48 may be used to limit the maximum torque applied to an element of the device, in order to prevent over-tightening and the like. Outer sleeve 48 includes a weakened, breakaway tab 49. Tab 49 may be placed within a keyway that is cut into the particular rotational-based piece, for example a keyway cut into a ratchet grip 10, 12. The tab 49 may include an irregular cross-section, such as the trapezoidal cross-section shown. The outer sleeve 48 and tab 49 may be slid over the ratchet grip 10 or 12 while sliding the tab 49 into the keyway. When a certain amount of torque is applied to the outer sleeve 48, the shear force between the keyway (and tab 49) and the outer sleeve 48 will cause separation or breakaway of the tab 49 from the sleeve 48 when it exceeds a certain amount. Upon separation of the tab 49 from the outer sleeve 48, the outer sleeve 48 simply rotates over the ratchet grip 10 or 12 without applying further torque, so as not to over-tighten the coil element 2 onto the lead 4, according to an embodiment of the present disclosure. In this way, standardizing the failure of the tab 49 at a known force or torque provides confirmation of a positive lock of the device 11 onto the lead 4. Based on the present disclosure, one of ordinary skill in the art will appreciate that other configurations for the tab and keyway are possible, and that other mechanisms may be used to achieve a similar function. For example, the ratchet grip 10 may include the tab, and the outer sleeve may include the keyway.

FIGS. 10 and 11 illustrate another embodiment of a ratchet deployment device 50. The ratchet deployment device 50 may in some embodiments include features and characteristics that are the same as or similar to device 11. That is, generally, the device 50 may include ratchet grips 51 and 52, a coil element 53, and a safety cap 54. The device 50 also includes a trailing wire or tether T. The tether T may include, for example, high strength braided fibers, metal wires, and the like. The tether T allows tension to be applied to the coil element 53 from a control point away from the coil element 53. Tether T extends further proximally than the lead when the device 50 is coupled with the lead. Tension applied to tether T is transmitted to the device 50 and thus to the lead when the device 50 is coupled to the lead. Tether T also permits an extraction device to be placed over it and advanced over the tether T to the device 50 and eventually to the lead to which device 50 is coupled. The tether T may be coupled to one or more of the ratchet grips 51 and 52 and the coil element 53. For example and as shown in FIGS. 10 and 11, the tether T extends through the inner lumen of the ratchet grip 52, into the inner lumen of the ratchet grip 51, and the ends of the tether T couple to the inner surface of the ratchet grip 51.

While FIGS. 10 and 11 illustrate the tether T coupled to a ratchet deployment device 50, such a tether T may be used with any of the types of devices disclosed herein. For example, the tether T illustrated in FIGS. 10 and 11 may be used with the cam actuation mechanism device 21 and/or a device including the outer sleeve 48.

Figure 12A:
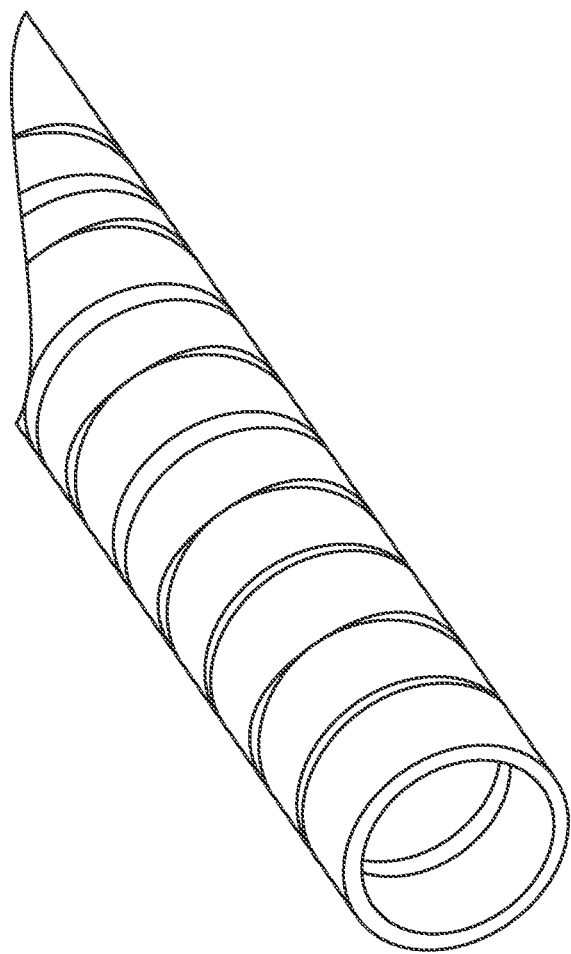
FIG. 12A illustrates a partial perspective view of a tubular member, according to an embodiment of the present disclosure.
Figure 12B:
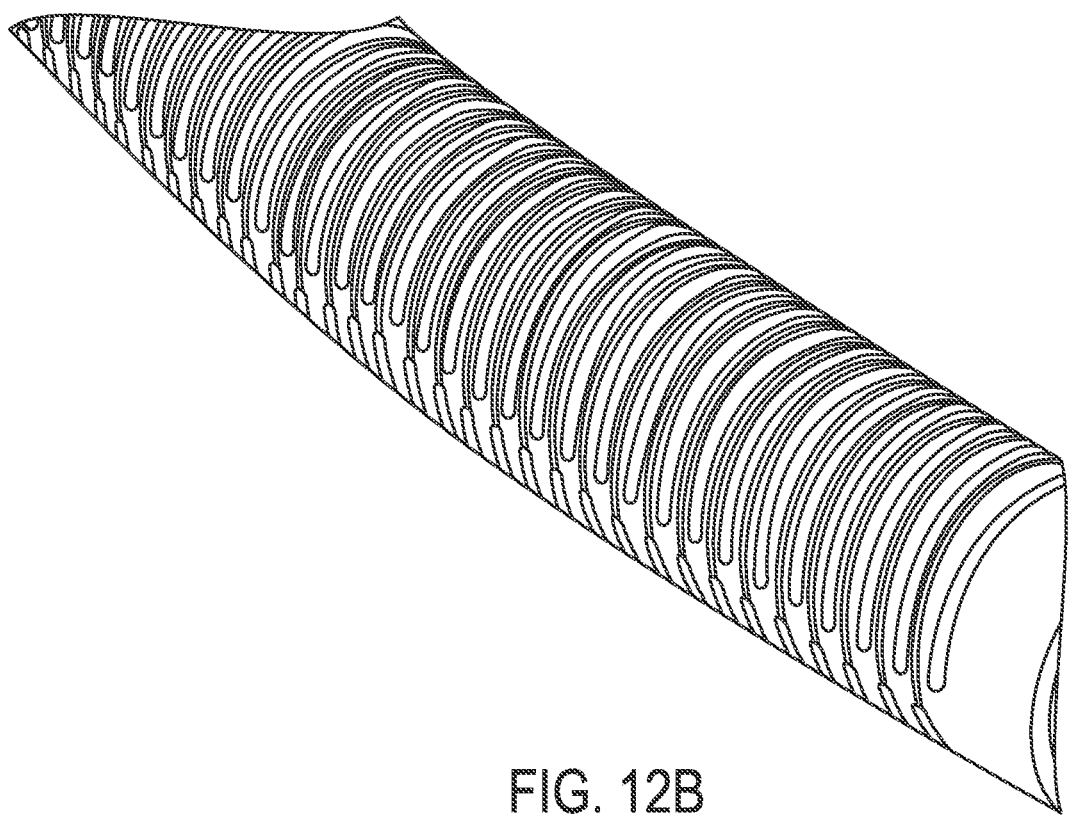
FIG. 12B illustrates a partial perspective view of a tubular member, according to an embodiment of the present disclosure.
Figure 12C:
FIG. 12C illustrates a top plan view of a tubular member, according to an embodiment of the present disclosure.
Figure 12D:
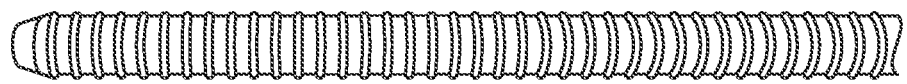
FIG. 12D illustrates a top plan view of the tubular member of FIG. 12C in an expanded configuration, according to an embodiment of the present disclosure.

A lead locking device for applying traction internally to a lead for lead removal is another example aspect of the present disclosure. A lead locking device employing a hollow tubular member, examples of which are shown in FIGS. 12A-12D, advantageously may also provide structure and rigidity internally along a substantial portion of the length or the entire length of a lead, thereby, increasing the chance for successful removal when used with an extraction device externally disposed relative to the lead. The tubular member is distortable in order to expand for locking or otherwise fixedly engage with the internal surface of a lead. An actuation mechanism effects the distortion and is releasable or reversible to return the distorted tubular member to its original shape as needed. Prior art lead locking devices that are not reversible may need to be abandoned within a lead if lead removal procedure proves unsuccessful. FIGS. 12A, 12B and 12C show some example configurations of tubular members, although as one of skill in the art would recognize, other tubular member configurations also are suitable. FIG. 12D is a distorted or expanded version of the tubular member of FIG. 12C.

Figure 13A:
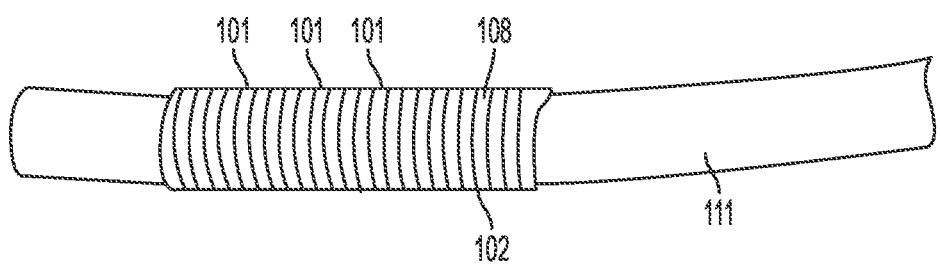
FIG. 13A illustrates a top plan view of a tubular member in an unexpanded configuration for sliding into a lead, according to an embodiment of the present disclosure.

FIG. 13A illustrates a top plan schematic view of a tubular member 102 (which may also be referred to as a hypotube) on a body 111 in a configuration for sliding into a lead (not shown), according to an embodiment of the present disclosure. In the configuration of FIG. 13A, the tubular member 102 includes a plurality of segments 101, and an outer surface 108 with an outer dimension or diameter that is small enough to be received by a lead therethrough, such that the tubular member 102 may be placed within the lead and/or slide freely within the lead when the tubular member 102 is in an unexpanded configuration as shown in this figure. The segment of tubular member 102 depicted may be a segment of a laser cut hypotube with an interrupted spiral cut ("ISC") pattern. The plurality of segments may be formed by, for example, ISC, coil cut pattern, and/or the like. The tubular member 102 may be expanded from the unexpanded configuration shown in FIG. 13A to the expanded configuration shown in FIG. 13B in which some or all of the plurality of segments 101 of the tubular member 102 are expanded, relaxed or released such that they engage and grip with an inner surface of a lead. In some embodiments, the expansion of the tubular member 102 results in compressive or expansive force being applied to the inner surface of the lead.

The tubular member 102 may be moved between a first configuration (e.g., unexpanded configuration) in which the tubular member 102 slides into or within a lead to a second configuration (e.g., expanded configuration) in which some or all of the segments of the tubular member 102 grippingly engage the inner surface of the lead in various ways. As one example, the tubular member 102 may be springably released, thereby causing the outer surface of the segments to expand to engage the lead. As another example, one end of the tubular member 102 may be rotated, twisted, or turned with respect to the other end of the tubular member 102 in order to forcibly, springably or naturally cause a loosening of the windings of the segments of the tubular member 102, thereby expanding their outer diameters to the point at which the tubular member engages the inner surface of the lead.

Figure 13B:
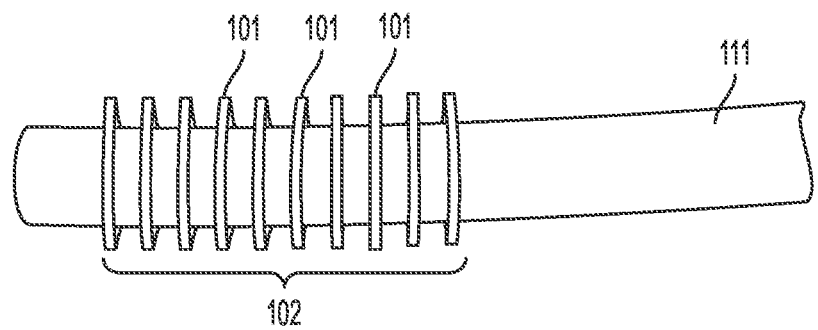
FIG. 13B illustrates a top plan view of the tubular member of FIG. 13A in an expanded configuration in which the segments of the tubular member engage an inner surface of a lead, according to an embodiment of the present disclosure.

FIG. 13B illustrates the tubular member 102 in an expanded configuration, in which the laser cut segment with interrupted spiral cut ("ISC") pattern has been expanded to engage the inner surface of a lead. A trailing wire or tether (not shown), including for example high strength braided fibers, metal wires, and the like, may be attached to the tubular member 102 to allow tension to be applied to the tubular member 102 from a control point away from the tubular member 102 and the lead itself. Tubular member 102 is made of a material suited for laser cutting, for example, stainless steel. Shape memory alloys are suitable for tubular member 102 including nickel titanium alloys. Other alloys including for example, nickel, titanium, copper, zine, aluminum, or combinations thereof, are suitable for tubular member 102 provided the alloy selected is biocompatible. Characteristics important in choosing the material for tubular member 102 include hardness and tensile strength. As tubular member sizes are required to be ever smaller for applications within patients' vessels, material selection is important to prevent tearing or pulling apart of the laser cut tubular member.

The tubular member includes a series of radially expandable, elastic sections that are substantially relaxed in the first configuration and radially expanded under a compressive force in the second configuration. In an example aspect, sections are uniformly repeated. In another example aspect, each section is variable. In another example aspect, two or more sections repeat alternatively. Sections may be cut or uncut. As one of skill in the art would recognize, each section can have various shapes. In an example aspect, sections include segments of various shapes or configurations such as, but not limited to, ring, spiral, diamond, parallel cuts, six-sided bodies, other such shapes, or combinations thereof. Sections may combine to form a helically oriented pathway including a plurality of open sections alternatingly disposed with bridge members so that if laid flat (or unrolled) the tubular member would appear as in one connected sheet. Varying pitches may be employed to provide sections of more rigidity or more flexibility. A tubular member configuration including varying cut patterns, sections, and pitches, some repeated, advantageously provide a tubular member configured to sequentially expand from one end of a length to the other, or alternatively from a section located within the tubular length or the middle of the tubular length to expand sequentially outwardly. For example, it may be desirable to deploy the tubular member to expand firstly at a tip to secure positioning, prior to sequentially expanding the tubular member to engage with the entire length of the lead inner surface thereby providing maximum traction.

In an example aspect of the present disclosure, a majority of the segments engage the inner lumen of the lead. In one embodiment, substantially all of the segments engage the inner lumen of the lead. The tubular member may be laser cut to achieve desired shape or pitch or both. Advantageously, the tubular member is releasable, repositionable, and reversible. In other words, the tubular member may be relaxed back to the first configuration, thus allowing for replacing or repositioning as necessary to provide the user with more control and better traction for removing, extending, or extracting the lead.

Figure 14A:
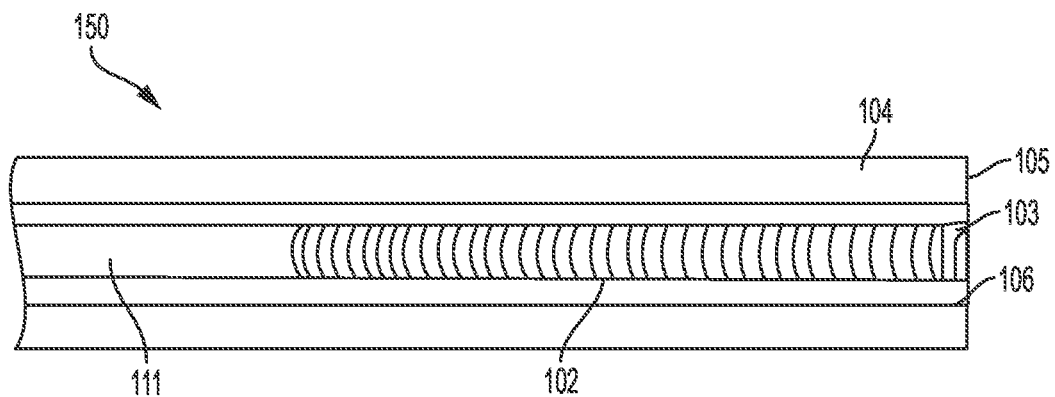
FIG. 14A illustrates a cross-sectional view of a tubular member disposed within a lead in an unexpanded configuration, according to an embodiment of the present disclosure.
Figure 14B:
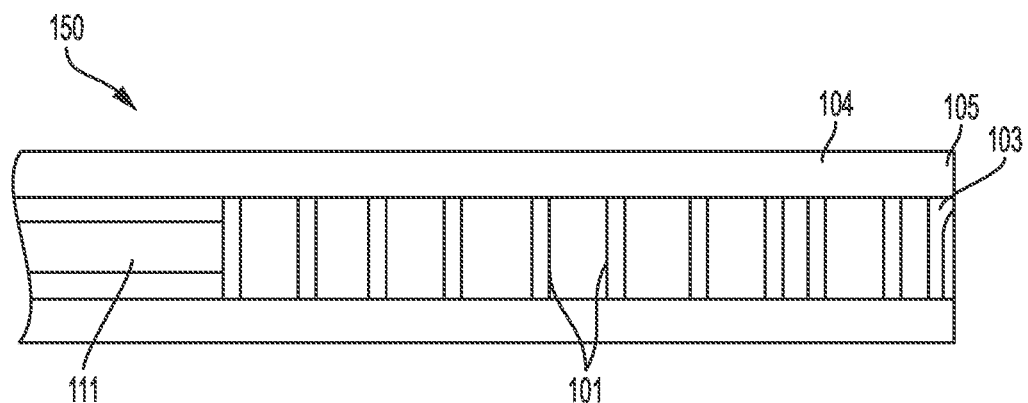
FIG. 14B illustrates a cross-section view of the tubular member of FIG. 14A in an expanded configuration in which the segments of the tubular member engage the inner surface of the lead, according to an embodiment of the present disclosure.

Referring to FIG. 14A and FIG. 14B, in an example aspect, a device for extending a lead is provided. The device 150 comprises body 111, tubular member 102 coupled to body 111. The tubular member 102 comprises an outer surface 108 (as shown in FIG. 13A), wherein the dimension(s) of the tubular member 102, including the outer surface, is sized to insert into inner lumen 106 of lead 105. Tubular member 102 is movable between a first configuration (e.g., unexpanded configuration) (as shown in FIG. 14A) in which the tubular member slides into or within lead 105, and a second configuration (e.g., expanded configuration) (as shown in FIG. 14B) in which at least a portion of tubular member 102 expands to engage inner surface 106 of lead 105.

In an example aspect, an actuation mechanism is operatively coupled to tubular member 102, wherein the actuation mechanism is configured to move the tubular member 102 between the first configuration and second configuration (and potentially back to the first configuration after the tubular member is in the second configuration). In an example aspect, the tubular member comprises a plurality of segments 101. In an example, at least some segments 101 of the plurality of segments springably release to sequentially engage inner surface 106 of lead 105 from a distal-most end 103 of the lead to a proximal-most end of the lead. In another example aspect, at least some segments 101 of the plurality of segments springably release to sequentially engage inner surface 106 of lead 105 from a proximal-most end of the lead to distal-most end 103 of the lead. In a further example, at least some segments 101 of the plurality of segments springably release to simultaneously engage the inner surface 106 of the lead 105. In an example aspect, the tubular member 102 includes a distal-most end that is aligned with a distal-most end of the lead 103. In an example aspect, the tubular member engages the entire longitudinal length of the lead.

Figure 15:
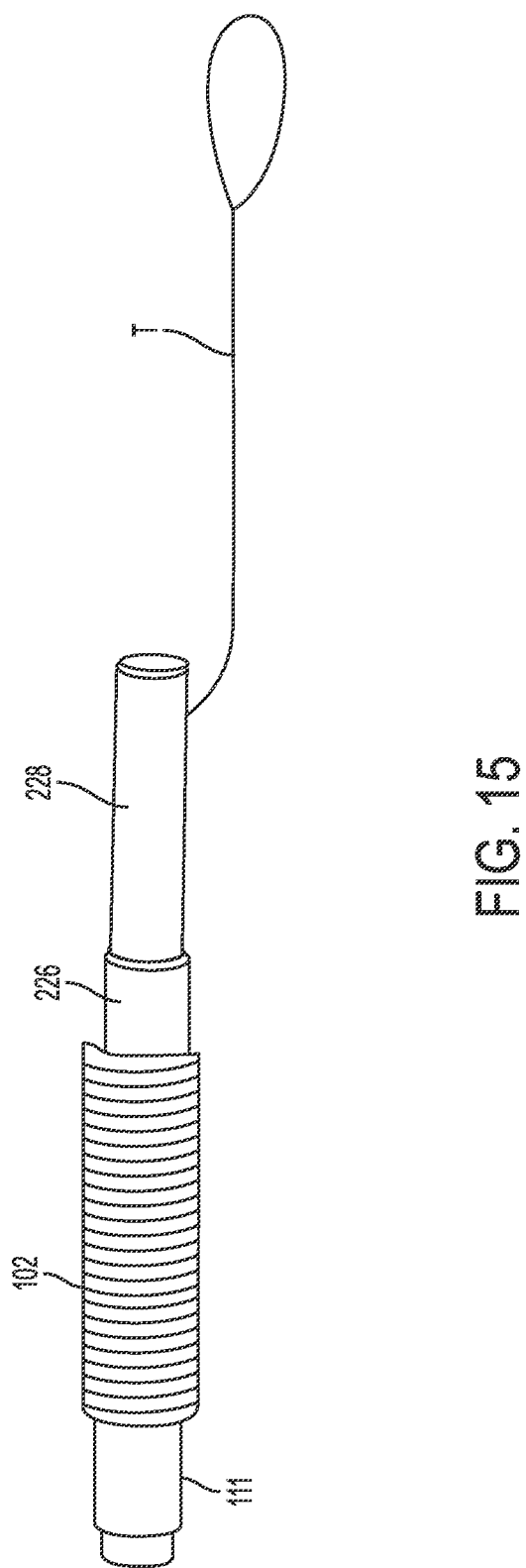
FIG. 15 illustrates a front elevation view of a ratchet body actuation mechanism for a tubular member for inserting within a lead, according to an embodiment of the present disclosure.

Different actuation mechanisms are employable to distort the tubular member including, but not limited to, friction or interference fit, slide coin, twist and deploy, or screw compression/extension mechanisms. FIG. 15 illustrates an embodiment wherein body 111 is a ratchet deployment device. In an example aspect, the ratchet deployment device includes inner sleeve 228 and outer sleeve 226 and, optionally, a trailing wire or tether T. The tether T may include, for example, high strength braided fibers, metal wires, and the like. The tether T allows tension to be applied to the tubular member 102 from a control point away from the tubular member 102. Tether T extends further proximally than the lead when the device is coupled with the lead. Tension applied to tether T is transmitted to the device and thus to the lead when the device is coupled to the lead. The tether T may be coupled to one or more of the ratchet grips 226 and 228 and the tubular member 102. While FIG. 15 illustrates the tether T coupled to a ratchet deployment device, such a tether T may be used with any of the types of devices disclosed herein. For example, the tether T illustrated in FIG. 15 may be used with a cam actuation mechanism device. In an example aspect, the device further comprises a tether coupled to a lead via one or more of the body, the tubular member, and the actuation mechanism, the tether configured to extend further proximally than a proximal-most end of the lead, the tether further configured to transfer at least a portion of a tension force applied to the tether to the lead via the one or more of the body, the tubular member, and the actuation mechanism.

Figure 16A:
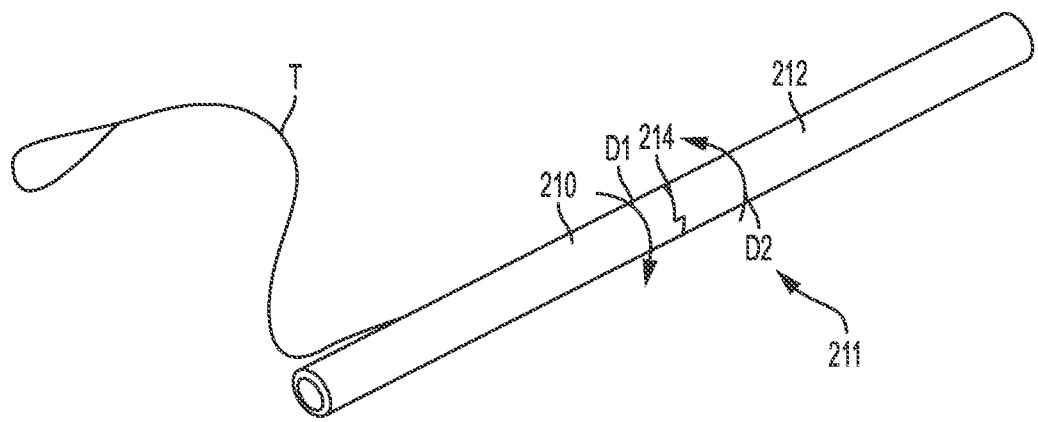
FIG. 16A illustrates a perspective view of a ratchet body actuation mechanism for a tubular member, according to an embodiment of the present disclosure.
Figure 16B:
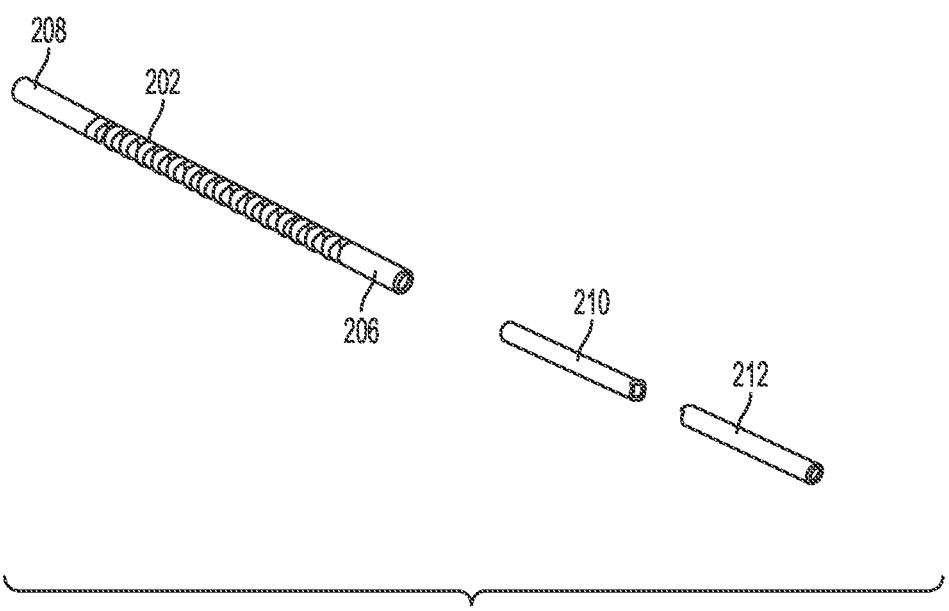
FIG. 16B illustrates an exploded view of the ratchet body actuation mechanism of FIG. 16A, according to an embodiment of the present disclosure.

FIG. 16A and FIG. 16B illustrate one embodiment of a ratchet deployment device 211, with an external laser-cut tubular member 202 and ratchet grips 210, 212. In the embodiment shown in FIGS. 16A and 16B, ratchet grip 210 is coupled to end 208 of tubular member 202 (e.g. by welding) within an interior lumen of tubular member 202, and ratchet grip 212 is coupled to end 206 of tubular member 202 (e.g. by welding) within an interior lumen of tubular member 202. Ratchet grips 210 and 212 interface with each other at unidirectional rotational coupling 214, which may be formed by teeth or other interengaging projections and indentations which permit ratchet grip 210 to rotate in direction D1 with respect to ratchet grip 212, and which permit ratchet grip 212 to rotate in direction D2 with respect to ratchet grip 210, but which inhibit rotation of such ratchet grips in respective directions opposite to those of D1 and D2 when the ratchet grips 210 and 212 are engaged with one another. In some embodiments, the first and second ratchet grips 210, 212 are biased toward one another, for example by the tubular member 202 acting as a spring. In other embodiments, the first and second ratchet grips 210, 212 are not biased together, but remain in place against one another based on the ability of the tubular member 202 to increase its outer diameter as it is twisted without elongating. The unidirectional rotational coupling mechanism may be referred to, in some cases, as a ratchet mechanism. The ratchet mechanism may be formed by teeth that are formed or cut into the ends of the ratchet grips 210, 212; such teeth may be undercut and/or back-cut, for example.

According to some embodiments of the present disclosure, the unidirectional rotational coupling is reversible and/or releasable. For example, for a tubular member 202 that has undergone elastic deformation in moving to the expanded configuration, pulling apart the first and second ratchet grips 210, 212 allows the release of one or both ratchet grips 210, 212, thereby permitting the tubular member 202 to rewind and springably disengage the lead. When the tubular member 202 is moved to the configuration in which it engages the lead, the tubular member 202 creates a relatively large force on the inner surface of the lead over a large area. In an example aspect, the tubular member is releasable and repositionable for further use. In other words, as the two ratchet grips 210, 212 are pushed together or pulled apart, the tubular member 202 may release the device 211 from the lead so that the device 211 can be repositioned and re-aligned within the lead body. According to some embodiments of the present disclosure, a bidirectional coupling may replace the unidirectional rotational coupling.

A tether T may be coupled to the body, for example to one of the first and second ratchet grips. As shown in FIG. 16A, a tether T is coupled to the ratchet grip 210 (length of tether T is not necessarily to scale). Tether T extends further proximally than the lead when the device 211 is coupled with the lead. Tension applied to tether T is transmitted to device 211 and thus to the lead when device 211 is coupled to the lead. Tether T also permits an extraction device to be placed over it and advanced over the tether T to device 211 and eventually to the lead to which device 211 is attached.

In an example aspect, the actuation mechanism comprises a first ratchet grip and a second ratchet grip, wherein the first ratchet grip is coupled to a first end of the tubular member, wherein the second ratchet grip is coupled to a second end of the tubular member. In an example aspect, the actuation mechanism is configured to move the tubular member between first and second configurations via one or both of the following: rotation of the first ratchet grip along a first rotational direction relative to the second ratchet grip; and rotation of the second ratchet grip along a second rotational direction relative to the first ratchet grip, wherein the first and second rotational directions are opposing rotational directions. In an example aspect, the first ratchet grip engages the second ratchet grip at a unidirectional rotational coupling that permits rotation of the first ratchet grip along the first rotational direction relative to the second ratchet grip and rotation of the second ratchet grip along the second rotational direction relative to the first ratchet grip while inhibiting rotation of the first ratchet grip along the second rotational direction relative to the second ratchet grip and of the second ratchet grip along the first rotational direction relative to the first ratchet grip while the first ratchet grip is in the unidirectional rotational coupling with the second ratchet grip. In an example aspect, the unidirectional rotational coupling includes one or more undercut or back-cut teeth formed on one or both of the first and second ratchet grips. In an example aspect, the first and second ratchet grips are axially separable from one another to release the unidirectional rotational coupling, thereby permitting the tubular member to move from a configuration in which the tubular member outer surface, having an outer diameter, is minimized to an expanded configuration.

In an example aspect, the device comprises an inner sleeve, a keyway formed in one of the inner sleeve and the first ratchet grip, and a tab formed in the other of the inner sleeve and the first ratchet grip, wherein torque is transmitted from the inner sleeve to the first ratchet grip via an interface between the keyway and the tab, the tab configured to break away from the inner sleeve at a level of applied torque. In an example aspect, the actuation mechanism is the body. The keyway and tab mechanism is similar as shown in FIG. 8 and FIG. 9.

Figure 17A:
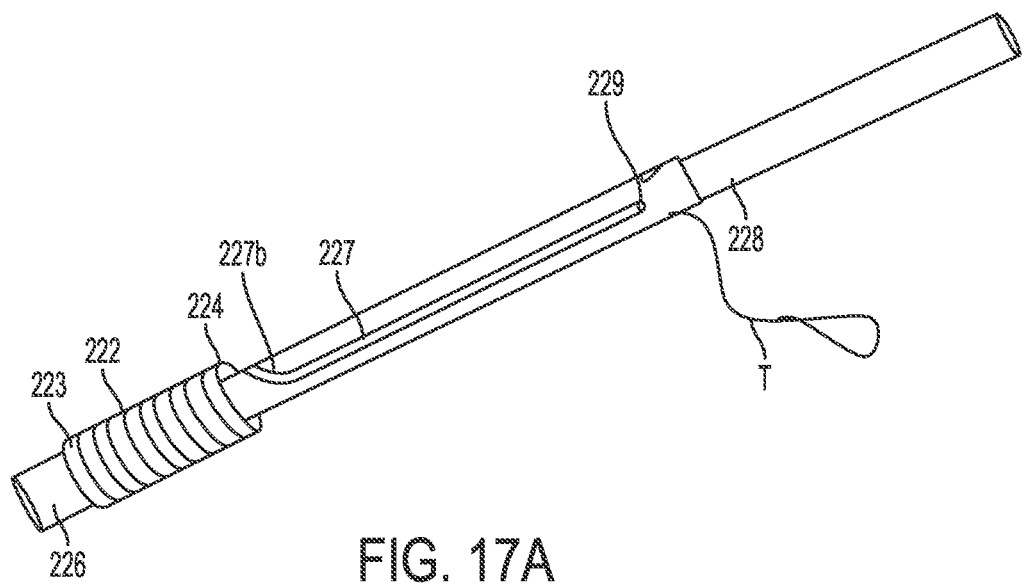
FIG. 17A illustrates a front perspective view of a cam actuation mechanism for a tubular member, according to an embodiment of the present disclosure.
Figure 17B:
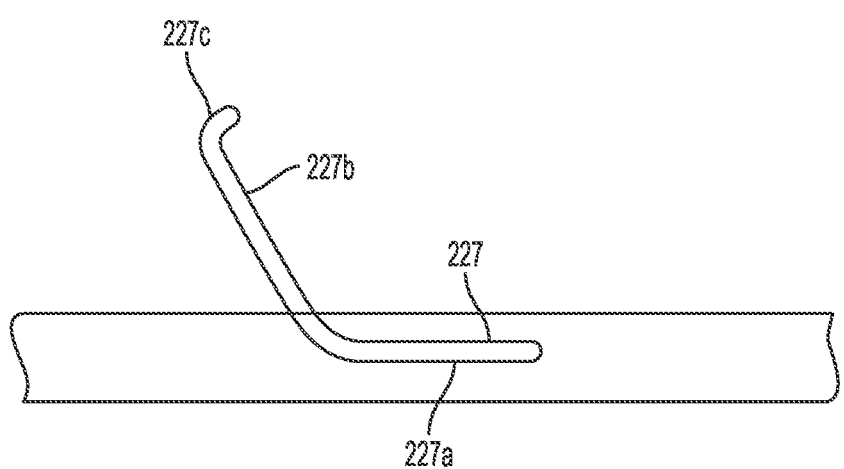
FIG. 17B illustrates a partial front elevation view of the cam actuation mechanism of FIG. 17A showing an unwound and flattened depiction of the cam pathway, according to an embodiment of the present disclosure.

FIG. 17A illustrates a front perspective view of a cam actuation mechanism device 221 for a tubular member 222, according to an embodiment of the present disclosure. FIG. 17B illustrates a partial front elevation view of the cam actuation mechanism device 221 of FIG. 17A showing an unwound and flattened depiction of the cam pathway 227, according to an embodiment of the present disclosure. The device 221 includes a tubular member 222, which may in some embodiments include features and characteristics that are the same as or similar to tubular member 202. Device 221 includes a body formed by an outer sleeve 226 and an inner sleeve 228; tubular member 222 is coupled to outer sleeve 226 at end 223 (e.g. by welding), and tubular member 222 is coupled to inner sleeve 228 at end 224 (e.g. by welding).

During operation, the tubular member 222 is placed within a lead, for example by placing the distal end 223 of tubular member 222 into the lead. In this first configuration, tubular member 222 has coils that have an outer diameter that is smaller than the diameter of the inner surface of the lead into which it is placed. Next, tubular member 222 may be moved to a second configuration in which some or all of the segments of tubular member 222 are springably released to engage in a gripping manner with the inner surface of the lead. This may be accomplished by moving the tubular member 222 longitudinally from a tightly wound configuration, for example along a longitudinal axis of the tubular member 222, which may be aligned with the longitudinal axis of the device 221 and the lead into which the device 221 is engaged. In the embodiment shown in FIG. 17A, the expanding of the tubular member 222 is achieved by translating the outer sleeve 228 toward the inner sleeve 226. The movement of the inner sleeve 226 with respect to the outer sleeve 228 may be governed by a cam actuation mechanism. The cam actuation mechanism of FIGS. 17A and 17B takes the form of a cam pathway 227 formed into the outer sleeve 226, within which is guided a pin 229 coupled to the inner sleeve 228. The cam pathway 227 may be formed of a slot extending through the outer sleeve 226 and/or of a groove formed within an inner surface of the outer sleeve 226, according to an embodiment of the present disclosure.

The cam pathway 227 may include various sections to achieve lengthening, expanding, and/or twisting of the tubular member 222, according to embodiments of the present disclosure. While one example of a cam pathway 227 is provided, one of ordinary skill in the art, who is familiar with the present disclosure, will appreciate the numerous possible cam pathways in order to move a tubular member 222 to a gripping engagement with a lead. Cam pathway 227 includes a first section 227a that extends along a substantially straight line that is substantially parallel to a longitudinal axis of the tubular member 222 and outer and inner sleeves 226, 228. A second section 27b generally continues to extend in a direction toward the tubular member 222, while also wrapping around the outer sleeve 226 in order to cause the inner sleeve 228 to twist or turn relative to the outer sleeve 226. A third section 227c causes the pin 229 to move away from the tubular member 222 while continuing to cause twisting of the inner sleeve 228 relative to the outer sleeve 226. According to some embodiments, the inner sleeve 226 is biased toward the outer sleeve 228 such that this biasing force is overcome when it is desired to push them together (thereby moving the tubular member 222 to the second/lead engaging position). Section 227c of the cam pathway 227 provides an endpoint in the second configuration in which the pin 229 can rest and in which the pin 229 is deterred from sliding back down the pathway sections 227b and 227a due to the biasing, according to an embodiment of the present disclosure. In this manner, Section 227c forms a locking mechanism which locks the pin 229 in the ending position and thereby locks the tubular member 222 in a configuration in which it is engaged in a gripping configuration with the lead.

A tether T may be optionally coupled to the body, for example to the outer sleeve 226, according to an embodiment of the present disclosure. As shown in FIG. 17A, a tether T is coupled to the outer sleeve 226 (length of tether T is not necessarily to scale). Tether T extends further proximally than the lead when the device 221 is coupled with the lead. Tension applied to tether T is transmitted to the device 221 and thus to the lead when the device 221 is coupled to the lead. Tether T also permits an extraction device to be placed over it and advanced over the tether T to the device 221 and eventually to the lead to which device 221 is attached.

In an example aspect of the present disclosure, the device includes a body comprising a first sleeve and a second sleeve, wherein the first sleeve is coupled to a first end of the tubular member, wherein the second sleeve is coupled to a second end of the tubular member, and wherein the actuation mechanism is configured to move the tubular member between the first and second configurations via axial translation of the first sleeve along a direction relative to the second sleeve. In an example aspect, the actuation mechanism further comprises a pin coupled to one of the first and second sleeves and a slot formed in another of the first and second sleeves, wherein the slot guides a path of translation of the first sleeve with respect to the second sleeve. In an example aspect, the slot includes a portion that imparts a tightening twist to the tubular member in moving the tubular member to the second configuration. In an example aspect, the direction is a first direction, and wherein the slot includes a portion that causes translation of the first sleeve along a second direction relative to the second sleeve in moving the tubular member to the second configuration, wherein the second direction is different from the first direction. In an example aspect, the second direction is opposite to the first direction. In an example aspect, the plurality of segments include segments of different pitch (as shown in FIG. 7), such that some of the plurality of segments are configured to expand to springably engage the lead at a lower applied torque than others of the plurality of segments. In another example, the actuation mechanism is configured for mechanical engagement. An inner sleeve having outwardly protruding dimples, for example, friction fits into the outer sleeve of the actuation mechanism. In an alternative example, the actuation mechanism friction fits to the tubular member. The actuation mechanism can be advantageously configured for bidirectional movement for deployment or distortion of the tubular member and for release or restoring the tubular member to original state.

In an example aspect of the present disclosure, a method is provided. The method includes extending a lead comprising the steps: sliding a tubular member into a lead when the tubular member is in a first configuration, the tubular member comprising an outer surface sized to insert into an inner lumen of the lead; moving the tubular member from the first configuration into a second configuration in which at least a portion of the tubular member expands to engage the inner lumen of the lead by actuating an actuation mechanism operatively coupled to the tubular member, the actuation mechanism configured to move the tubular member between the first configuration and the second configuration. In an example aspect of the method, the tubular member comprises a plurality of segments. In an example aspect of the method, at least some segments of the plurality of segments springably release to sequentially engage the inner surface of the lead from a distal-most end of the lead to a proximal-most end of the lead or from a proximal-most end of the lead to a distal-most end of the lead. In an example aspect of the method, the actuation mechanism comprises a first ratchet grip and a second ratchet grip, wherein the first ratchet grip is coupled to a first end of the tubular member, wherein the second ratchet grip is coupled to a second end of the tubular member, and wherein manipulating the actuation mechanism to move the tubular member from the first configuration into the second configuration includes one or both of: rotating the first ratchet grip along a first rotational direction relative to the second ratchet grip, and rotating the second ratchet grip along a second rotational direction relative to the first ratchet grip, wherein the first and second rotational directions are opposing rotational directions. In an example aspect of the method, the tubular member includes a first end coupled to a first sleeve and a second end coupled to a second sleeve, and wherein manipulating the actuation mechanism to move the tubular member from the first configuration into the second configuration includes translating the first sleeve along a direction relative to the second sleeve. In an example aspect of the method, the actuation mechanism further comprises a pin coupled to one of the first and second sleeves and a slot formed in another of the first and second sleeves, the slot guiding a path of translation of the first sleeve with respect to the second sleeve, and wherein manipulating the actuation mechanism to move the tubular member from the first configuration into the second configuration causes the slot to impart a releasing twist to the tubular member. In an example aspect of the method, the plurality of segments include segments of a first pitch and segments of a second pitch, and moving the tubular member from the first configuration into the second configuration includes releasing the segments of the first pitch to springably engage the inner lumen of the lead at a first applied torque and releasing the segments of the second pitch to springably engage the inner lumen of the lead at a second applied torque, the second applied torque being less than the first applied torque.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure may be used. It would be possible to provide for some features of the disclosure without providing others.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A lead locking device, comprising:
   a tubular member configured to engage a lead;
   a first ratchet grip coupled to the tubular member; and
   a second ratchet grip coupled to tubular member,
   wherein the first ratchet grip and the second ratchet grip are configured to interface with one another at a rotational coupling,
   wherein the rotational coupling is configured to:
      permit rotation of the first ratchet grip relative to the second ratchet grip in a first direction; and
      inhibit rotation of the first ratchet grip relative to the second ratchet grip in an opposite, second direction.

2. The device of claim 1, wherein the tubular member is configured to be positioned internally relative to the first ratchet grip and the second ratchet grip.

3. The device of claim 1, wherein the tubular member comprises a coil.

4. The device of claim 1,
   wherein the tubular member comprises a first end and an opposite, second end,
   wherein the first ratchet grip is coupled to the first end, and
   wherein the second ratchet grip is coupled to the second end.

5. The device of claim 1, wherein the rotational coupling comprises:
   a first engagement feature of the first ratchet grip; and
   a second engagement feature of the second ratchet grip.

6. The device of claim 5, wherein the first engagement feature is positioned at a first end of the first ratchet grip and the second engagement feature is positioned at an opposite second end of the second ratchet grip.

7. The device of claim 5, wherein the first engagement feature and the second engagement feature each comprise at least one of a projection or an indentation.

8. The device of claim 7, wherein the projection comprises an undercut tooth or back-cut tooth.

9. The device of claim 1, wherein the first ratchet grip and the second ratchet grip are biased toward one another.

10. The device of claim 1, wherein the first ratchet grip and the second ratchet grip are not biased toward one another.

11. The device of claim 1, wherein the rotational coupling is reversible.

12. The device of claim 11, wherein the first ratchet grip and the second ratchet grip are configured to be pulled apart such that the tubular member is configured to release the lead.

13. The device of claim 1, further comprising a safety cap configured to be positioned over the rotational coupling.

14. The device of claim 13, wherein the safety cap is coupled to the first ratchet grip or the second ratchet grip.

15. The device of claim 1, further comprising a tether coupled to the first ratchet grip or the second ratchet grip.

* * * * *